(12) United States Patent
Hasegawa et al.

(10) Patent No.: US 9,074,973 B2
(45) Date of Patent: Jul. 7, 2015

(54) CLOTH EVALUATION APPARATUS

(75) Inventors: Kenji Hasegawa, Tokyo (JP); Nobuhisa Ito, Tokyo (JP)

(73) Assignee: YKK Corporation (JP)

( * ) Notice: Subject to any disclaimer, the term of this patent is extended or adjusted under 35 U.S.C. 154(b) by 57 days.

(21) Appl. No.: 13/814,376

(22) PCT Filed: Aug. 6, 2010

(86) PCT No.: PCT/JP2010/063418
§ 371 (c)(1),
(2), (4) Date: Feb. 5, 2013

(87) PCT Pub. No.: WO2012/017557
PCT Pub. Date: Feb. 9, 2012

(65) Prior Publication Data
US 2013/0125663 A1    May 23, 2013

(51) Int. Cl.
*G01N 3/00* (2006.01)
*G01N 3/60* (2006.01)
*D06H 1/00* (2006.01)
*G01N 3/58* (2006.01)
(Continued)

(52) U.S. Cl.
CPC .. *G01N 3/60* (2013.01); *D06H 1/00* (2013.01); *G01N 2203/0019* (2013.01); *G01N 2203/0053* (2013.01); *G01N 2203/0067* (2013.01); *G01N 2203/0282* (2013.01); *G01N 3/58* (2013.01); *G01N 33/367* (2013.01); *G01N 3/24* (2013.01); *G01N 3/42* (2013.01); *G01N 2203/0206* (2013.01); *G01N 2203/02* (2013.01); *G01B 21/08* (2013.01)

(58) Field of Classification Search
CPC .............................. G01N 33/367; G01N 11/12
USPC ........................................................... 73/839
See application file for complete search history.

(56) References Cited

U.S. PATENT DOCUMENTS 1,452,944 A * 4/1923 Webb .............................. 73/839
2,522,544 A * 9/1950 Seyboth ......................... 73/839
(Continued)

FOREIGN PATENT DOCUMENTS

EP        0823438 A2    2/1998
FR        687 819 A      8/1930
(Continued)

OTHER PUBLICATIONS

International Search Report, PCT Application No. PCT/JP2010/063418, mailed Sep. 28, 2010.
(Continued)

*Primary Examiner* — Harshad R Patel
(74) *Attorney, Agent, or Firm* — Kilpatrick Townsend & Stockton LLP

(57) ABSTRACT

A cloth evaluation apparatus can grasp the piercing property and the cutting property with a cloth in advance. The cloth evaluation apparatus includes a measuring member having, on its distal side, a measuring part to pass through a cloth; a cloth/measuring part moving means for moving the cloth or the measuring member so that the measuring part passes through the cloth; a cloth supporting means for supporting the cloth at around a passing-through point, in the cloth, of the measuring part from both sides of the cloth when the measuring part passes through the cloth; and a load detecting means for detecting a load being applied to the measuring member while the measuring part passes through the cloth.

12 Claims, 18 Drawing Sheets

(51) Int. Cl.
*G01N 3/24* (2006.01)
*G01N 3/42* (2006.01)
*G01N 33/36* (2006.01)
*G01B 21/08* (2006.01)

(56) References Cited

U.S. PATENT DOCUMENTS

| | | | |
|---|---|---|---|
| 3,541,843 A | 11/1970 | Flesher | |
| 3,548,647 A * | 12/1970 | Zacios | 73/839 |
| 3,618,372 A * | 11/1971 | Beckstrom | 73/839 |
| 3,793,881 A * | 2/1974 | Hallock, Jr. | 73/839 |
| 5,813,277 A | 9/1998 | Schmidt et al. | |
| 6,152,003 A * | 11/2000 | Jung | 83/74 |
| 2004/0103528 A1 | 6/2004 | Okada | |
| 2010/0043565 A1 | 2/2010 | Shimizu | |

FOREIGN PATENT DOCUMENTS

| | | |
|---|---|---|
| FR | 2569849 A1 | 3/1986 |
| GB | 160 619 A | 3/1921 |
| JP | 61-282468 A | 12/1986 |
| JP | 2-161335 A | 6/1990 |
| JP | 8-062109 A | 3/1996 |
| JP | 9-236527 A | 9/1997 |
| JP | H10 2814 A | 1/1998 |
| JP | 2989589 B1 | 12/1999 |
| JP | 2002-327328 A | 11/2002 |
| JP | 2009-000224 A | 1/2009 |

OTHER PUBLICATIONS

International Preliminary Report on Patentability, PCT Application No. PCT/JP2010/063418, mailed Mar. 12, 2013.
Protective Clothing Mechanical Properties Determination of the Resistance to Puncture, GB/T 20655-2006/ISO 13996, 1999.
Office Action, Chinese Patent Application No. 2010800694309, Nov. 25, 2014.
Supplementary European Search Report, European Patent Application No. 10855646.5, mailed Apr. 22, 2015.

* cited by examiner

CLOTH EVALUATION APPARATUS

This application is a national stage application of PCT/JP2010/063418 which is incorporated herein by reference.

BACKGROUND OF THE INVENTION

The present invention relates to a cloth evaluation apparatus, and more particularly relates to a cloth evaluation apparatus for measuring and evaluating the piercing property and the cutting property with respect to a cloth in order to preliminary know the suitability in mounting a button or an eyelet onto various cloths using a mounting member.

When a button, an eyelet or the like (hereinafter referred to as merely "button") is mounted onto a cloth of clothing etc., a sharp part of a mounting member is passed through the cloth and then is plastically deformed on the button. More particularly, after the button is held by an upper die above the cloth as is horizontally placed, and the mounting member is set on a lower die below the cloth, the upper die is lowered by operating a press machine. Thereby, the sharp part of the mounting member pierces the cloth upward and then is swaged on the button by the upper die (a punch thereof). As a result, the button is fixed to the cloth. If a button is mounted to a certain cloth using an unsuitable mounting member, mounting defects such that the button easily comes off the cloth would be caused. Therefore, conventionally, the suitability or the unsuitability of a mounting member or a combination of a button and a mounting member with respect to a cloth is determined by preliminary knowing the cloth thickness at the time of applying a predetermined pressure to the cloth by using a cloth thickness measuring apparatus as disclosed in Japanese Patent No. 2989589.

However, even though a combination of a cloth and a mounting member (and a button) is judged to be suitable on the basis of the cloth thickness under a predetermined pressure, it is known that mounting defects with the button would be caused. This is mainly relevant to the material, weaving, knitting, overlapping, etc. of a cloth and how a sharp part of a mounting member passes through the cloth (a cloth passing-through manner). As cloth passing-through manners of a sharp part of a mounting member, generally there are a) "piercing," where the tip of a sharp part sticks a point on the cloth and then the sharp part expands a grain of the cloth while piercing the cloth, and b) "cutting," where a tip face of a sharp part pushes a part of the cloth in the passing direction and then separate or cut the part from the cloth. The piercing property with a cloth when a sharp part of a mounting member is "piercing" the cloth or a force for piercing the cloth, or the cutting property with a cloth when a sharp part is "cutting" the cloth or a force for passing through the cloth can vary depending on the material, weaving, knitting, overlapping, etc. of a cloth even if the thickness of each cloth under a predetermined pressure is same. This is seemed to influence a mounting property of a button.

[Patent Document 1] Japanese Patent No. 2989589

SUMMARY OF THE INVENTION

In view of the problems as mentioned above, an object of the present invention is to provide a cloth evaluation apparatus which can grasp the piercing property and the cutting property with a cloth in advance.

To solve the above-mentioned problems, according to the invention, there is provided a cloth evaluation apparatus comprising: a measuring member having, on its distal side, a measuring part to pass through a cloth; a cloth/measuring part moving means for moving the cloth or the measuring member so that the measuring part passes through the cloth; a cloth supporting means for supporting the cloth at around a passing-through point, in the cloth, of the measuring part from both sides of the cloth when the measuring part passes through the cloth; and a load detecting means for detecting a load being applied to the measuring member while the measuring part passes through the cloth, wherein the measuring part includes a piercing force measuring portion whose outer diameter gradually decreases toward its acute tip and, after the tip sticks the cloth, the piercing force measuring portion can pass through the cloth while expanding a grain of the cloth.

In the invention, a "cloth" includes sheet-like materials such as textile, fabric, nonwoven fabric, felt, leather, resin sheet and the like to which a button can be mounted.

In the invention, the measuring part of the measuring member is passed through the cloth, and during the passing the load being applied to the measuring member is detected by the load detecting means in real time. After the tip of the piercing force measuring portion of the measuring part sticks a point on the cloth, the piercing force measuring portion can pass through the cloth while expanding a grain of the cloth. At this time, the load just before the tip of the piercing force measuring portion comes through the cloth is specified and evaluated as the piercing force with the cloth. The passing through the cloth of the measuring part of the measuring member is carried out by the cloth/measuring part moving means moving one of the measuring member and the cloth to the other. As the cloth/measuring part moving means, for example, a mechanism in which, when an operator grips an operation lever or actuates a motor, a mover is moved via a drive transmitting mechanism can be quoted, but not limited thereto. When the measuring part of the measuring member passes through the cloth, the cloth is pushed from both sides by a cloth supporting means. Thereby, the cloth is prevented from being taken along by the measuring part. The cloth/measuring part moving means can doubly serve as a part of the cloth supporting means. As a part of the cloth supporting means, an elastic member can be used which can follow the displacement of the cloth with respect to the measuring part of the measuring member. Further, as the load detecting means, a pressure sensor such as a load cell or the like can be preferably used, but not limited thereto.

According to another aspect of the invention, there is provided a cloth evaluation apparatus comprising: a measuring member having, on its distal side, a measuring part to pass through a cloth; a cloth/measuring part moving means for moving the cloth or the measuring member so that the measuring part passes through the cloth; a cloth supporting means for supporting the cloth at around a passing-through point, in the cloth, of the measuring part from both sides of the cloth when the measuring part passes through the cloth; and a load detecting means for detecting a load being applied to the measuring member while the measuring part passes through the cloth, wherein the measuring part includes a cutting force measuring portion having a shear face which can push a part of the cloth in the passing direction to separate the part from the cloth as the measuring part passes through the cloth.

In the invention, the measuring part of the measuring member is passed through the cloth, and during the passing the load being applied to the measuring member is detected by the load detecting means in real time. The cutting force measuring portion of the measuring part can press a part of the cloth (cloth part) in the passing direction by the shear face at the time of passing through the cloth and separate the part. At this time, the load just before the shear face of the cutting force measuring portion separates the cloth part is specified and evaluated as the cutting force with the cloth.

According to still another aspect of the invention, a cloth evaluation apparatus comprising: a measuring member having, on its distal side, a measuring part to pass through a cloth; a cloth/measuring part moving means for moving the cloth or the measuring member so that the measuring part passes through the cloth; a cloth supporting means for supporting the cloth at around a passing-through point, in the cloth, of the measuring part from both sides of the cloth when the measuring part passes through the cloth; and a load detecting means for detecting a load being applied to the measuring member while the measuring part passes through the cloth, wherein the measuring part includes a piercing force measuring portion whose outer diameter gradually decreases toward its acute tip and, after the tip sticks the cloth, the piercing force measuring portion can pass through the cloth while expanding a grain of the cloth, wherein the measuring part includes a cutting force measuring portion adjacent proximally to the piercing force measuring portion, the cutting force measuring portion having a shear face which can push a part of the cloth in the passing direction to separate the part from the cloth as the measuring part passes through the cloth.

In the invention, after the tip of the piercing force measuring portion of the measuring part sticks a point on the cloth, the piercing force measuring portion can pass through the cloth while expanding a grain of the cloth. Then, the cutting force measuring portion of the measuring part can press a part of the cloth (cloth part) in the passing direction by the shear face at the time of passing through the cloth and separate the part. At this time, the load just before the tip of the piercing force measuring portion comes out of the cloth is specified and evaluated as the piercing force with the cloth, and the load just before the shear face of the cutting force measuring portion separates the cloth part is specified and evaluated as the cutting force with the cloth.

In an embodiment of the invention, the cutting force measuring portion includes an annular depression with a decreased outer diameter between the proximal end of the piercing force measuring portion and the shear face, the outer diameter of the proximal end being maximum in the piercing force measuring portion, and a surface, in the annular depression, on the proximal side of the measuring member serves as the shear face. In this case, the cloth part, which has been spread out by the proximal end, with the maximal diameter, of the piercing force measuring portion, restores to come into the depression adjacent proximally to the proximal end. Thereby, the cutting force measuring portion can securely capture the cloth portion to be separated.

In an embodiment of the invention, the cloth evaluation apparatus includes a displacement detecting means for detecting a displacement amount of the measuring part with respect to the cloth. By real-time detecting the amount of displacement of the measuring part with respect to the cloth, it is possible to associate the change in the load as being applied to the measuring member between the time when the measuring part contacts the cloth and the time when the measuring part finishes passing through the cloth with the position of the measuring part within the interval between one side and the other side of the cloth. As a displacement detecting means, a displacement sensor such as a pulse coder and the like, or a position sensor and the like can be preferably used, but not limited thereto.

In an embodiment of the invention, the measuring part includes a cloth thickness measuring portion, to compress the cloth, proximally from the cutting force measuring portion. The cloth thickness measuring portion compresses the cloth without passing through the cloth and measures the cloth thickness at the time when this compression force reaches the predetermined value. This cloth thickness can be obtained from the detection value from the displacement detecting means at the time when the detection value from the load detecting means reaches the predetermined compression force (for example, 200 N).

In an embodiment of the invention, the cloth supporting means includes an elastic member which can support the cloth while following the movement of the cloth or the measuring member. With such an elastic member, it is possible to always push one side of the cloth at around a passing-through point. As an elastic member, a cylindrical rubber, a coil spring and the like can be preferably used.

According to another aspect of the invention, there is provided a cloth evaluation apparatus comprising: a measuring member having, on its distal side, a measuring part to pass through or compress a cloth; a cloth/measuring part moving means for moving the cloth or the measuring member so that the measuring part passes through or compresses the cloth; a cloth supporting means or supporting the cloth at around a passing-through point, in the cloth, of the measuring part from both sides of the cloth when the measuring part passes through the cloth or from one side of the cloth when the measuring part compresses the cloth from the other side of the cloth; a load detecting means for detecting a load being applied to the measuring member while the measuring part passes through or compresses the cloth; and a displacement detecting means for detecting a displacement amount of the measuring part with respect to the cloth, wherein as the measuring member, a first measuring member and a second measuring member can be exchangeably used, wherein the measuring part of the first measuring member is a piercing force measuring portion whose outer diameter gradually decreases toward its acute tip and, after the tip sticks the cloth, the piercing force measuring portion can pass through the cloth while expanding a grain of the cloth, wherein the measuring part of the second measuring member is a cutting force measuring portion having a shear face which can push a part of the cloth in the passing direction to separate the part from the cloth as the measuring part passes through the cloth. In this case, either of the first measuring member having only the piercing force measuring portion or the second measuring member having only the cutting force measuring portion can be suitably chosen to be used.

In an embodiment of the invention, as the measuring member, the first measuring member, the second measuring member and a third measuring member can be exchangeably used, and the measuring part of third the measuring member is a cloth thickness measuring portion to compress the cloth. In this case, either of the first measuring member having only the piercing force measuring portion or the second measuring member having only the cutting force measuring portion or the third measuring member having only the cloth thickness measuring portion can be suitably chosen to be used.

According to still another aspect of the invention, there is provided a cloth evaluation apparatus comprising: a measuring member having, on its distal side, a measuring part to pass through or compress a cloth; a cloth/measuring part moving means for moving the cloth or the measuring member so that the measuring part passes through or compresses the cloth; a cloth supporting means for supporting the cloth at around a passing-through point, in the cloth, of the measuring part from both sides of the cloth when the measuring part passes through the cloth or from one side of the cloth when the measuring part compresses the cloth from the other side of the cloth; a load detecting means for detecting a load being applied to the measuring member while the measuring part passes through or compresses the cloth; and a displacement detecting means for detecting a displacement amount of the measuring part with respect to the cloth, wherein as the measuring member, a first measuring member and a second measuring member can be exchangeably used, wherein the measuring part of the first measuring member includes a piercing force measuring portion whose outer diameter gradually decreases toward its acute tip and, after the tip sticks the cloth, the piercing force measuring portion can pass through the cloth while expanding a grain of the cloth, and the measuring part includes a cutting force measuring portion adjacent proximally to the piercing force measuring portion, the cutting force measuring portion having a shear face which can push a part of the cloth in the passing direction to separate the part from the cloth as the measuring part passes through the cloth, and wherein the measuring part of the second measuring member is a cloth thickness measuring portion to compress the cloth. In this case, either of a first measuring member having only the piercing force measuring portion or a second measuring member having only the cutting force measuring portion or a third measuring member having only the cloth thickness measuring portion can be suitably chosen to be used. In this case, either of the first measuring member having the piercing force measuring portion and the cutting force measuring portion or the second measuring member having only the cloth thickness measuring portion can be suitably chosen to be used.

In the present invention, the piercing force measuring portion and/or the cutting force measuring portion of the measuring member is passed through the cloth, and at this time the load just before the tip of the piercing force measuring portion comes out of the cloth is rated as the piercing force with the cloth, and the load just before the shear face of the cutting force measuring portion separates the cloth part is rated as the cutting force with the cloth. Thereby, the piercing property and cutting property with the cloth can be easily grasped in advance. Therefore, whether a button can be mounted suitably or not to a certain cloth using a mounting member can be known in advance at a high accuracy.

DETAILED DESCRIPTION OF THE INVENTION

Figure 1:
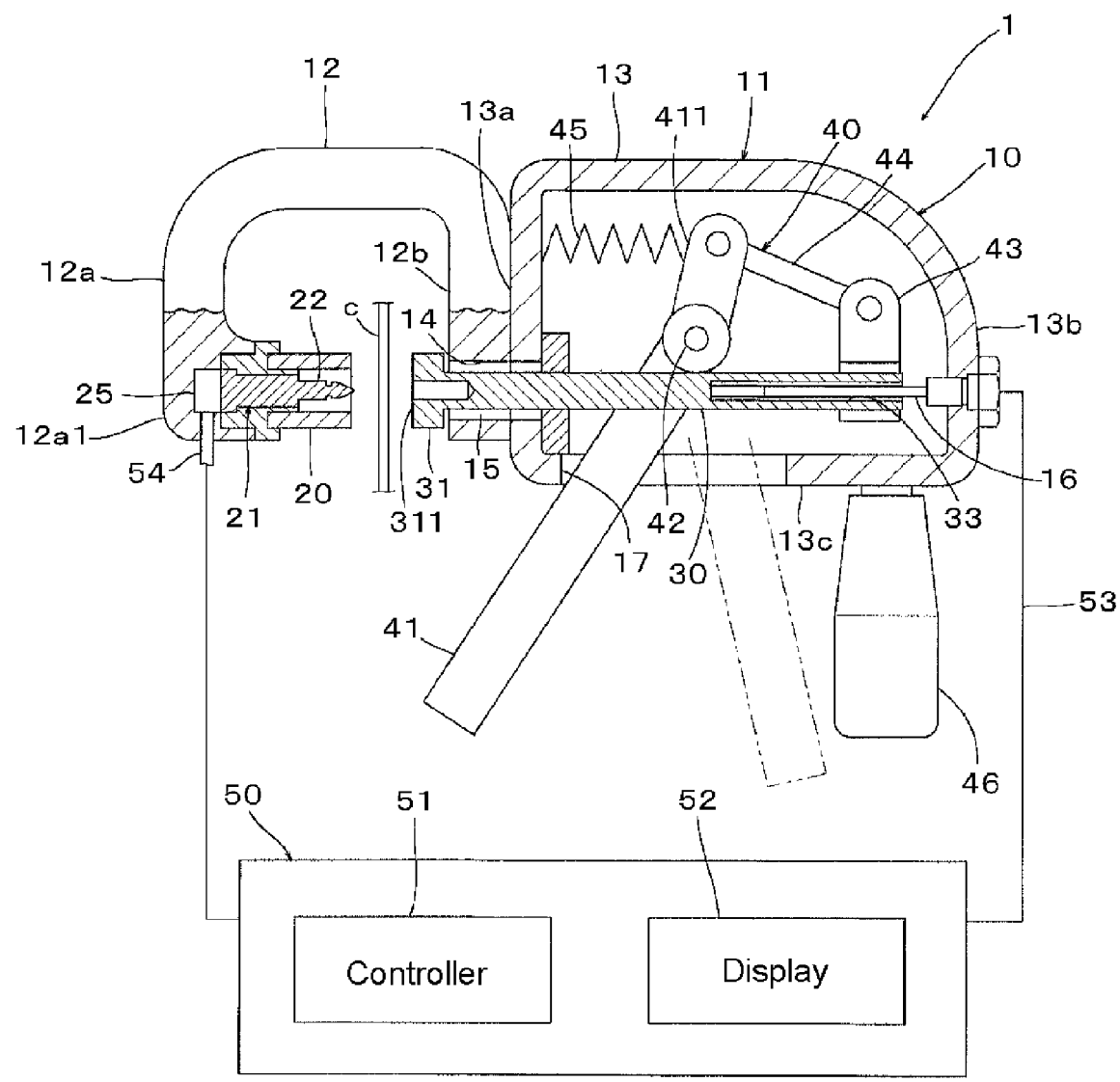
FIG. 1 is a partially sectional schematic configuration view showing a cloth evaluation apparatus in accordance with one embodiment of the invention.

Hereinafter, preferable embodiments of the invention will be described with reference to the drawings. FIG. 1 is a schematic configuration view of a cloth evaluation apparatus 1 in accordance with one embodiment of the invention. The cloth evaluation apparatus 1 is composed of: a lever handle measuring unit 10, which can be operated by an operator with one hand; and a control box 50 for processing load and displacement detecting signals, as mentioned later, which are input from the measuring unit 10. The control box 50 includes a microcomputer base controller 51 having CPU, ROM, RAM, input and output interfaces (including A/D converters, D/A converters, amplifiers, etc.), a display 52 for displaying results processed by the controller 51, a power source circuit (not shown) and the like.

The measuring unit 10 comprises: a stationary section 20 which includes a measuring member 21 having a measuring part 22 which is tapered and almost columnar and which will be passed through a cloth c in order to evaluate the piercing property, the cutting property and the like of the cloth c; an elongated columnar bar-like mover 30 which is arranged concentrically with the measuring part 22 in the stationary section 20 and which can be moved toward the measuring part 22; a mover driving mechanism 40 which can move the mover 30 forwardly (on the left side in FIG. 1) from an initial position shown in FIG. 1 (hereinafter referred to "the initial position" as to the mover 30 and an operation lever 41 in FIG. 1) toward the stationary section 20 by an operator gripping the operation lever 41; and a frame body 11 which integrally supports the stationary section 20, the mover 30 and the mover driving mechanism 40. The mover 30 and the mover driving mechanism 40 constitute a cloth/measuring member moving means. Hereinafter, unless front and rear directions are otherwise specified, the left side and the right side in FIG. 1 are referred to as front and rear, respectively. Upper and lower directions are also based on FIG. 1. The frame body 11 is composed of a front frame 12 which is a reversed U-shaped frame and a box-like rear frame 13 (its side is opened in FIG. 1). The front and rear frames 12 and 13 are integrated such that a rear arm 12b of the front frame 12 and a front wall 13a of the rear frame 13 are welded. The stationary section 20 is provided at a lower end 12a1 of a front arm 12a of the front frame 12 such that the tip 22A1 of the measuring part 22 of the measuring member 21 faces rearward, as described in detail later. The mover 30 is supported by a bearing 15 provided in an opening 14 which passes through a lower portion of the rear arm 12b of the front frame 12 and the front wall 13a of the rear frame 13 continuously in the front and rear direction. The bearing 15 allows the mover 30 to be moved forward and rearward. In a rear portion of the mover 30, there is formed a hollow 33. A spline shaft 16 is conformably inserted into the hollow 33, the spline shaft 16 extending forward from a rear wall 13b of the rear frame 13 in a cantilever manner. Thereby, the mover 30 is supported by the spline shaft 16 such that the mover 30 cannot be rotated. A pulse coder 161 as a displacement detecting means is incorporated in the spline shaft 16 for real-time detecting displacement amounts from the initial position of the mover 30. The pulse coder 161 is connected through a signal line 53 to the controller 51 in the control box 50.

Further, the mover 30 has a pusher 31 to push the cloth c forward, which is exposed in front of the rear arm 12b of the front frame 12. The pusher 31 is a thick circular plate-like portion having the outer diameter greater than that of the mover 30 except for the pusher 31, and cannot pass through the bearing 15 in the opening 14. The front surface of the pusher 31 serves as a pushing surface 311 to push the cloth c. The pushing surface 311 constitutes a part of a cloth supporting means. In the pusher 31, there is formed a columnar cavity 32 extending rearward from a center portion on the pushing surface 311, and the columnar cavity 32 is for receiving the measuring part 22 which has passed through the cloth c at the time of measuring as described later.

The mover driving mechanism 40 includes: the operation lever 41 which protrudes downwardly through an opening 17 of a bottom wall 13c of the rear frame 13; a fixed shaft 42 for rotatably supporting the operation lever 41; a driving transmitter 43 which is fixed onto the rear end of the mover 30; and a link 44 which is interposed between an upper portion 411 of the operation lever 41 (hereinafter referred to as "lever upper portion") and the driving transmitter 43 in order to transmit the motion of the operation lever 41 to the driving transmitter 43. The lever upper portion 411 is slightly angled with respect to the operation lever 41 except for the lever upper portion 411. The mover driving mechanism 40 further includes a spring 45 between the lever upper portion 411 and the front wall 13a of the rear frame 13. The spring 45 pushes the lever upper portion 411 rearward (in the clockwise direction) and sets the operation lever 41 as in in a non-operational state, in the initial position. A reference numeral 46 indicates a fixed grip which extends downward from the bottom wall 13c of the rear frame 13. To operate the operation lever 41, an operator grips the operation lever 41 with the thumb holding the fixed grip 46. When an operator grips the operation lever 41 from the FIG. 1 state, the operation lever 41 is rotated in the counterclockwise direction around the fixed shaft 42 as the center, and the lever upper portion 411 is displaced forward (in the counterclockwise direction) against the pushing force of the spring 45. With this displacement, the link 44 pulls the driving transmitter 43 forward, causing the mover 30 to move forward. After that, when the operator releases the operation lever 41, the spring 45 recovers so as to push the lever upper portion 411 rearward. Then, in a contrary manner to the above mentioned one, the link 44 and the driving transmitter 43 are displaced rearward, returning the mover 30 backward.

Figure 2:
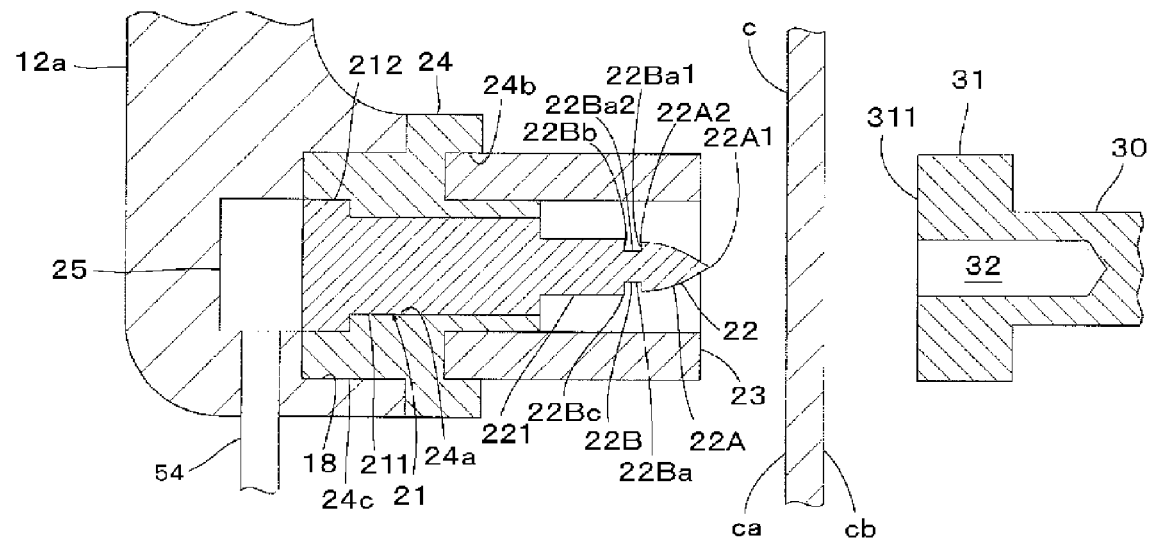
FIG. 2 is a sectional explanation view showing a stationary section and a pusher of a mover facing to each other with a cloth between them.

With reference to FIG. 2, the stationary section 20 comprises: the measuring member 21 which is exchangeable and has the measuring part 22; a cylindrical elastic member 23 made of urethane rubber and the like, which is arranged around and concentrically with the measuring part 22 of the measuring member 21; and an almost cylindrical attachment 24 which supports an almost columnar proximal portion 211 of the measuring member 21 and a proximal portion of the elastic member 23 and detachably fixes the measuring member 21 and the elastic member 23 to a stationary section fixing part 18 which is formed on the lower end 12a1 of the front arm 12a of the front frame 12. The elastic member 23 constitutes a part of the cloth supporting means and can always push the cloth c at around a passing-through point on the stationary section 20-side surface ca of the cloth c over a period while the pusher 31 of the mover 30 pushes the cloth c forward and the measuring part 22 passes through the cloth c rearward. Hereinafter, the front surface or the stationary section 20-side surface ca of the cloth c is referred to as "first surface ca," and the rear surface or the mover 30-side surface is referred to as "second surface cb." The outer diameter of the proximal portion 211 of the measuring member 21 is greater than that of the measuring part 22 and is constant (except for a diameter-expanded portion 212), and the proximal portion 211 includes on its proximal end the diameter-expanded portion 212 whose outer diameter is further expanded in a stepped manner. The attachment 24 includes a measuring member supporting part 24a for conformably receiving the proximal portion 211 including the diameter-expanded portion 212 of the measuring member 21, an elastic member receiving part 24b for receiving the proximal portion of the elastic member 23, and a frame connecting part 24c for detachably connecting to the stationary section fixing part 18 of the front frame 12 such as by a threaded manner, a press-fitted manner and the like. The axial length of the measuring member supporting part 24a of the attachment 24 is equal to the axial length of the proximal portion 211 of the measuring member 21. A stepped boundary between the proximal portion 211 received in the measuring member supporting part 24a and the measuring part 22 is flush with the distal end surface of the attachment 24. The stationary section 20 includes a load cell 25 as a load detecting means, which is disposed adjacent to the bottom surface of the measuring member 21 behind its diameter-expanded portion 212 (on the side opposite to the measuring part 22). The load cell 25 can detect in real time the load of the measuring member 21 being pushed proximally at the time of measuring. The load cell 25 is connected through a signal line 54 to the controller 51 in the control box 50.

The measuring part 22 of the measuring member 21 includes on the distal side the piercing force measuring portion 22A for detecting the piercing force with the cloth c; a cutting force measuring portion 22B for detecting the cutting force with the cloth c, which is formed adjacent proximally to the piercing force measuring portion 22A, and a measuring part-proximal portion 221 which is columnar and whose outer diameter is constant. The piercing force measuring portion 22A has an acute tip 22A1 and a piercing force measuring portion-proximal end 22A2. The outer diameter of the piercing force measuring portion 22A gradually increases proximally from the tip 22A1 and becomes maximum at the piercing force measuring portion-proximal end 22A2.

The piercing force measuring portion 22A can pass through the cloth c while expanding a grain of the cloth c after sticking a point on the cloth c by the tip 22A1. The cutting force measuring portion 22B includes an annular depression 22Ba in which its diameter is decreased in a stepped manner on the proximal side of the piercing force measuring portion-proximal end 22A2 (on the proximal side with respect to the measuring member 21), the cross-section of the depression 22Ba being rectangular. The depression 22Ba is defined by a distal face 22Ba1, a shear face 22Bb or a proximal face, and a depression bottom face 22Ba2 which extends parallel to the axis of the measuring member 21 between the radially inner ends of the distal face 22Ba1 and the shear face 22Bb. The outer diameter of the measuring part-proximal portion 221 of the measuring member 21 is slightly greater than that of the piercing force measuring portion-proximal end 22A2. At the periphery of the shear face 22Bb, an edge 22Bc is formed which is defined by the shear face 22Bb and the outer surface of the measuring part-proximal portion 221 of the measuring member 21. When the cutting force measuring portion 22B passes through the cloth c, the portion 22B can receive a part c1 (see FIG. 6) of the cloth c in the depression 22Ba, and then separate the part c1 from the cloth c by the shear face 22Bb pushing the part c1 in the passing direction.

Next, a state of using the cloth evaluation apparatus 1 as configured above will be described below. Firstly, the cloth c as a measuring target is vertically arranged between the stationary section 20 and the pusher 31 of the mover 30. Then, by the operator griping the operation lever 41, the mover 30 is moved forward from the initial position via the mover driving mechanism 40, and then the pushing surface 311 of the pusher 31 pushes the cloth c against the measuring part 22 of the measuring member 21 of the stationary section 20. Thereby, the measuring part 22 passes through the cloth c rearward. At the time of passing, the load being applied to the measuring member 21 is detected by the load cell 25, and the displacement amount from the initial position of the mover 30 is detected by the pulse coder 161. These detection signals are real-time sent through the signal lines 54, 53 to the controller 51, and the measurement results are displayed on the display 52. The foregoing measuring operation can be completed in only several seconds after the operator starts to handle the operation lever 41. The process of the measuring part 22 of the measuring member 21 passing through the cloth c will be described below in more detail.

Figure 3:
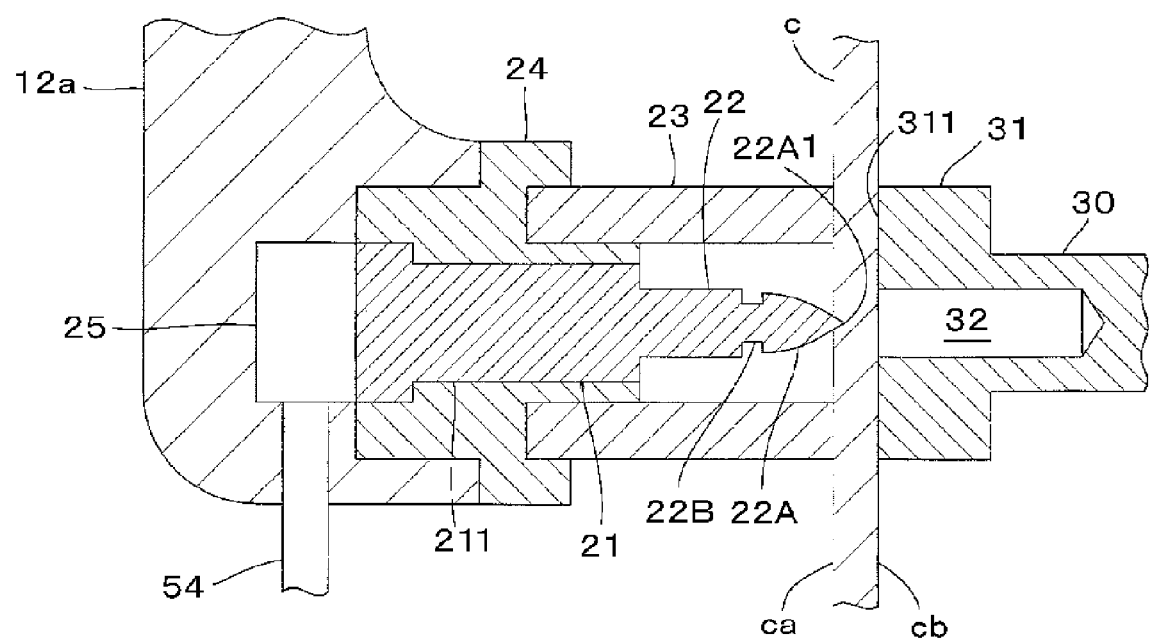
FIG. 3 is a sectional explanation view showing a point of time when a piercing force measuring portion sticks one side of the cloth.
Figure 4:
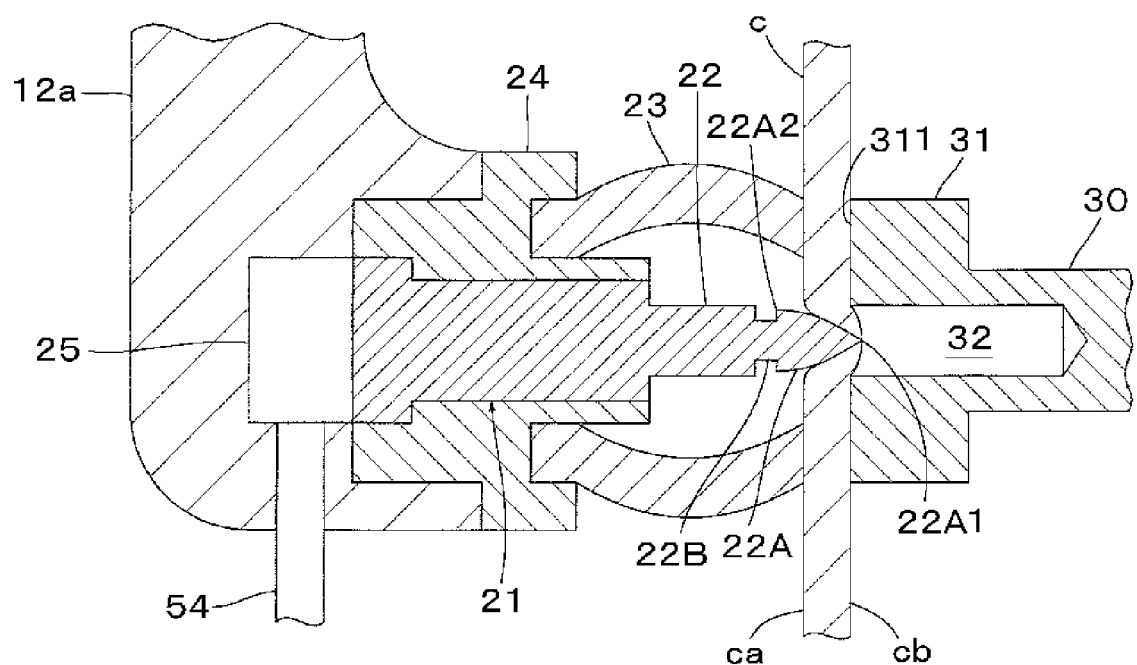
FIG. 4 is a sectional explanation view showing a state just before the piercing force measuring portion comes through the cloth.
Figure 5:
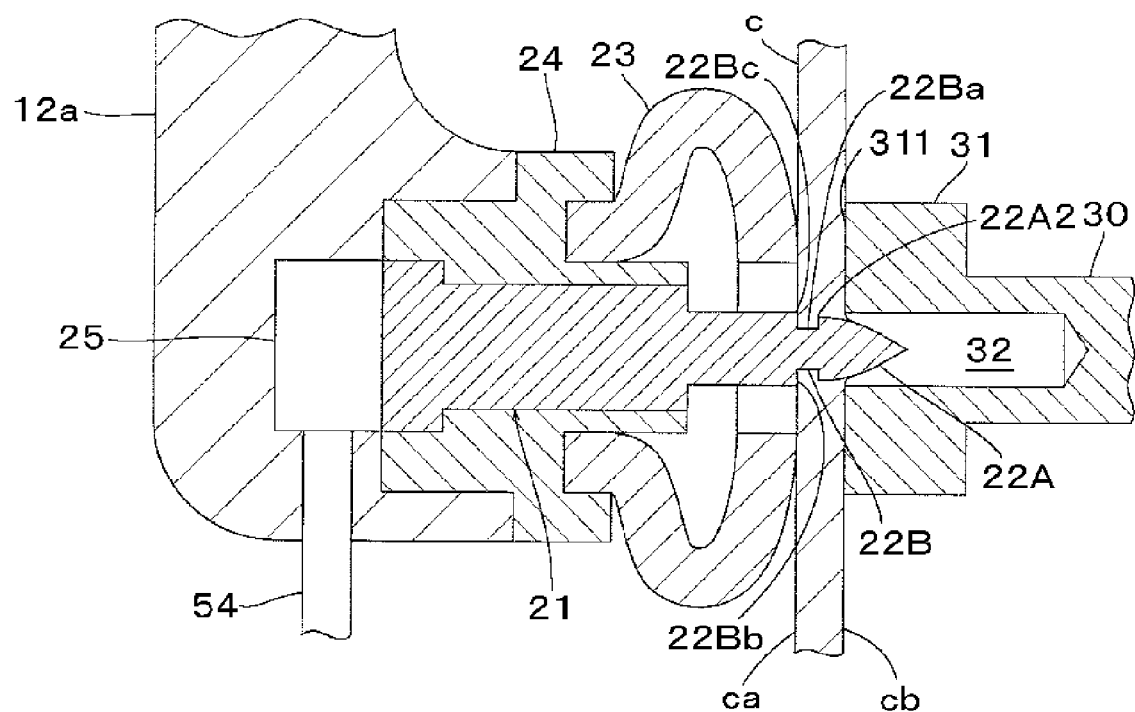
FIG. 5 is a sectional explanation view showing a state where a part of the cloth comes into a depression of the cutting force measuring portion after the piercing force measuring portion comes through the cloth.
Figure 6:
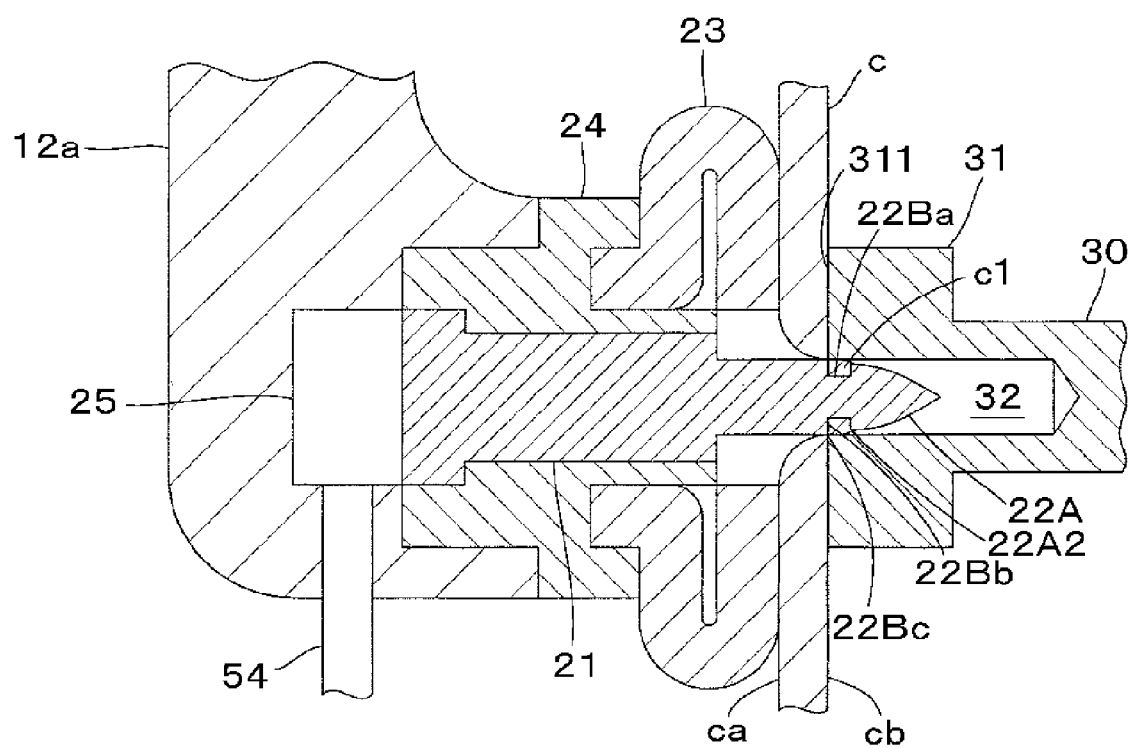
FIG. 6 is a sectional explanation view showing a state just after the cutting force measuring portion has passed through the cloth.
Figure 7:
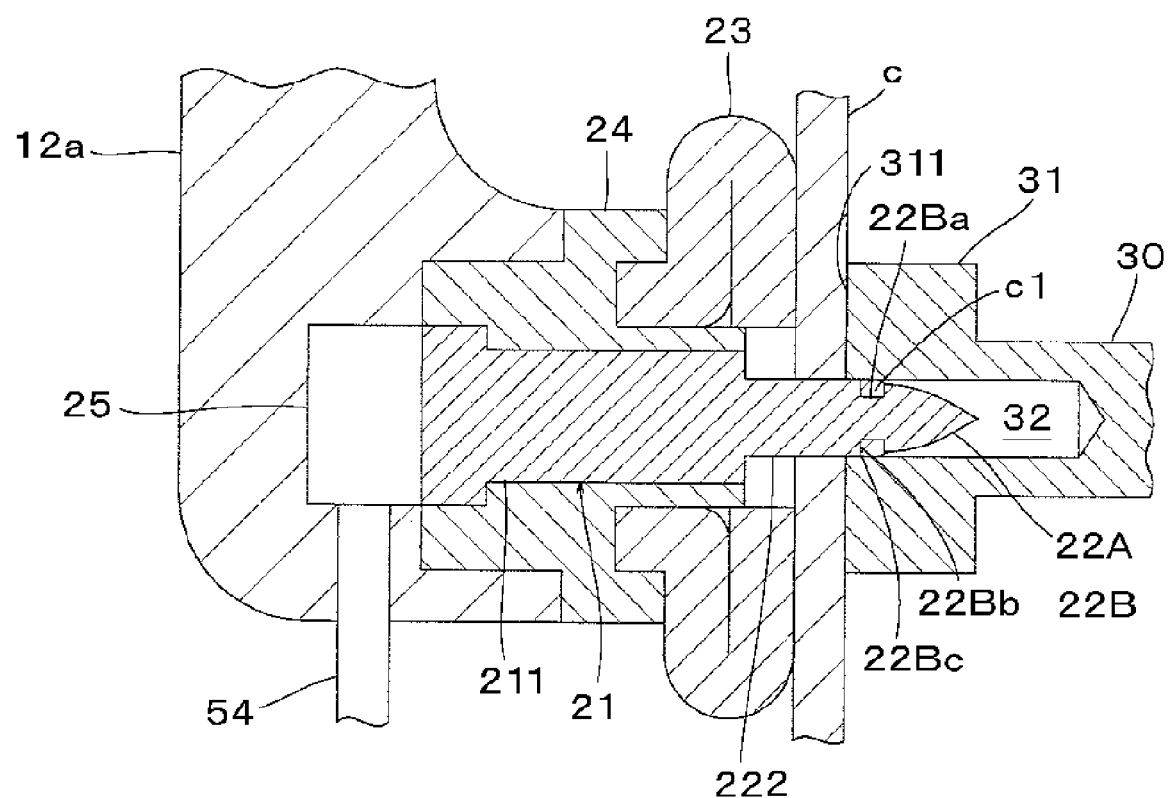
FIG. 7 is a sectional explanation view showing a state where the pusher of the mover is inhibited from further moving by a deformed elastic member after the cutting force measuring portion passes through the cloth.

FIG. 3 shows a state where the tip 22A1 of the piercing force measuring portion 22A of the measuring part 22 sticks a point on the first surface ca of the cloth c as the pushing surface 311 of the pusher 31 of the mover 30 pushes the cloth c forward. At this time, the elastic member 23 of the stationary section 20 supports the cloth c at around a passing-through point (expected) on the first surface ca of the cloth c. The pushing surface 311 of the pusher 31 supports a peripheral part of the passing-through point on the second surface cb of the cloth c while pushing the cloth c forward. As the cloth c is pushed forward by the pusher 31 from the FIG. 3 state, the piercing force measuring portion 22A moves relatively rearward (in the passing direction) in the cloth c while expanding a grain of the cloth c as shown in FIG. 4. Also at this time, the pushing surface 311 of the pusher 31 begins compressing the elastic member 23 via the cloth c. The elastic member 23 supports the first surface ca of the cloth c while expanding radially outward and shrinking axially. Therefore, the cloth c cannot be taken along rearward by the piercing force measuring portion 22A. When the cloth c is further pushed forward from the FIG. 4 state, as shown in FIG. 5, the tip 22A1 of the piercing force measuring portion 22A comes through the cloth c rearward and comes into the cavity 32 of the pusher 31. At this time, following the piercing force measuring portion 22A, the cutting force measuring portion 22B comes in the cloth c. Then, a cloth part c1, which has been spread out by the piercing force measuring portion-proximal end 22A2, restores to come into the depression 22Ba of the cutting force measuring portion 22B. As the cutting force measuring portion 22B moves relatively rearward, the cloth part c1 which has come in the depression 22Ba is pushed rearward by the shear face 22Bb of the depression 22Ba against the pushing surface 311 of the pusher 31 and then cut away from the cloth c by the edge 22Bc of the depression 22Ba. As shown in FIG. 6, the cut cloth part c1, staying in the depression 22Ba, is conveyed into the cavity 32 of the pusher 31. At this time, the elastic member 23 keeps supporting the first surface ca of the cloth c while further expanding radially outward and shrinking axially. FIG. 7 shows a state where the cutting force measuring portion 22B completes the passing through the cloth c and the elastic member 23 is completely crushed in the axial direction. At this time, the mover 30 is restrained from moving forward any further.

Figure 8:
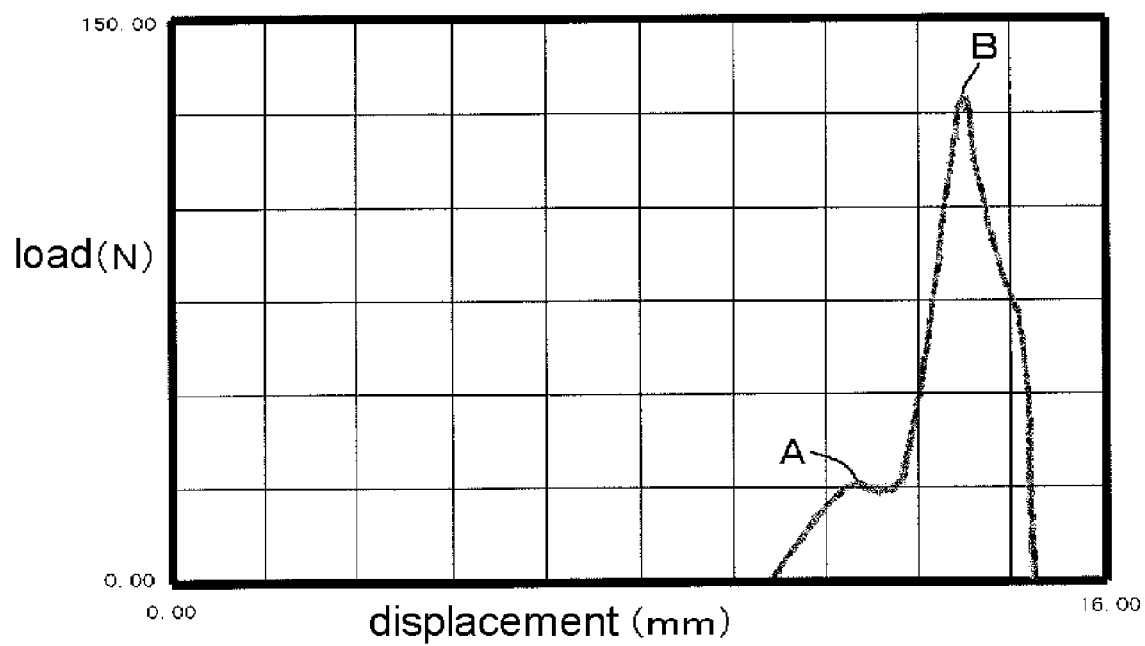
FIG. 8 is a graph showing the results of measuring the cloth piercing force and the cloth cutting force.

FIG. 8 is a graph showing results of the controller 51's processing of the load and displacement detecting signals from the load cell 25 and the pulse coder 16, the graph being displayed on the display 52. In the graph, the amount of displacement (mm) from the initial position of the mover 30 is taken on the lateral axis, and the load (N) being applied to the measuring member 21 is taken on the vertical axis, respectively. Until the tip 22A1 of the measuring member 21 contacts the cloth c after the mover 30 begins moving from the initial position, the load applied to the measuring member 21 is zero. After the cloth c is made contact with the tip 22A1 of the measuring member 21, the load begins to be detected, and the load increases as the cloth c is displaced forward. However, when the tip 22A1 of the piercing force measuring portion 22A has just pierced the cloth c (in the FIG. 4 to FIG. 5 state), the increase in the load stops, and then the load slightly decreases. A small peak value A which is the start point of this change is rated as the pulling force with the cloth c. Just after the change, when the shear face 22Bb and the edge 22Bc of the cutting force measuring portion 22B is cutting the cloth part c1 in the depression 22Ba from the cloth c, the load sharply increases. Then, once the cloth part c1 is separated from the cloth c (in the FIG. 5 to FIG. 6 state), the load sharply decreases. This peak value B is rated as the cutting force with the cloth c.

Figure 9:
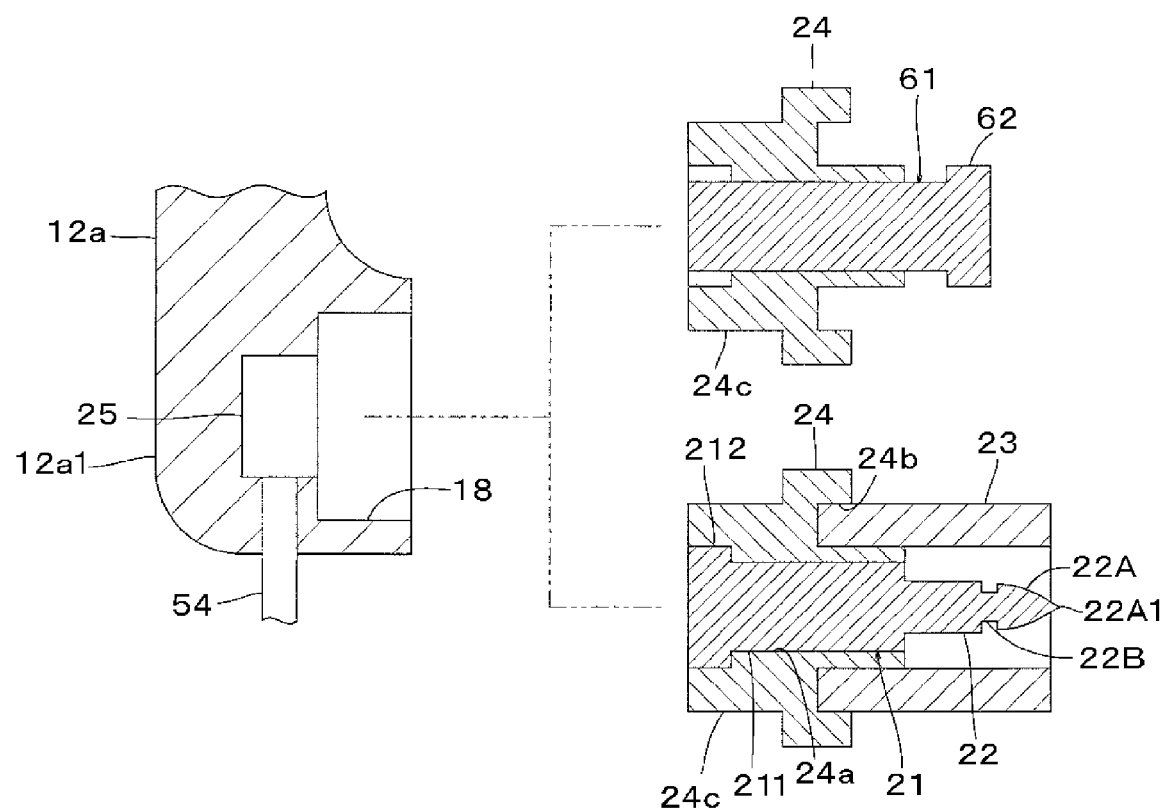
FIG. 9 is a sectional explanation view showing two measuring members which can be exchangeably mounted to a stationary section fixing part via an attachment.

FIG. 9 is a sectional explanation view showing two kinds of the measuring members 21, 61, each of which can be exchangeably attached to the stationary section fixing part 18 of the front frame 12 via the same attachment 24. The measuring member 21 is one as described above with the piercing force measuring portion 22A and the cutting force measuring portion 22B. The measuring member 61 is one for measuring the thickness of the cloth c at the time of applying a predetermined pressure thereto. To use the measuring member 21, the tip 22A1 of the measuring member 21 is passed through the measuring member supporting part 24a of the attachment 24 from the attachment's proximal side to the distal side, and the proximal portion 211 of the measuring member 21 including the diameter-expanded portion 212 is fitted in the measuring member supporting part 24a. Then, the frame connecting part 24c of the attachment 24 is connected to the stationary section fixing part 18. Before or after this connecting, the proximal portion of the elastic member 23 is inserted into the elastic member receiving part 24b. The measuring member 61 has, on its distal side, a cloth thickness measuring portion 62 whose diameter is somewhat expanded. The cloth thickness measuring portion 62 can compress the cloth c against the pushing surface 311 of the pusher 31 of the mover 30 without passing through the cloth c. To use the measuring member 61 having the cloth thickness measuring portion 62, the proximal end of the measuring member 61 is inserted into the measuring member supporting part 24a of the attachment 24 form the attachment's distal side to the proximal side, and then the frame connecting part 24c of the attachment 24 is connected to the stationary section fixing part 18. The measuring member 61 can be attached to the attachment 24 after the frame connecting part 24c is connected to the stationary section fixing part 18. The measuring member 61 does not have, on its proximal side, a diameter-expanded portion like the diameter-expanded portion 212 of the measuring member 21. Further, when the measuring member 61 is used, the elastic member 23 for pushing the cloth c at the time of passing is not needed.

Figure 10:
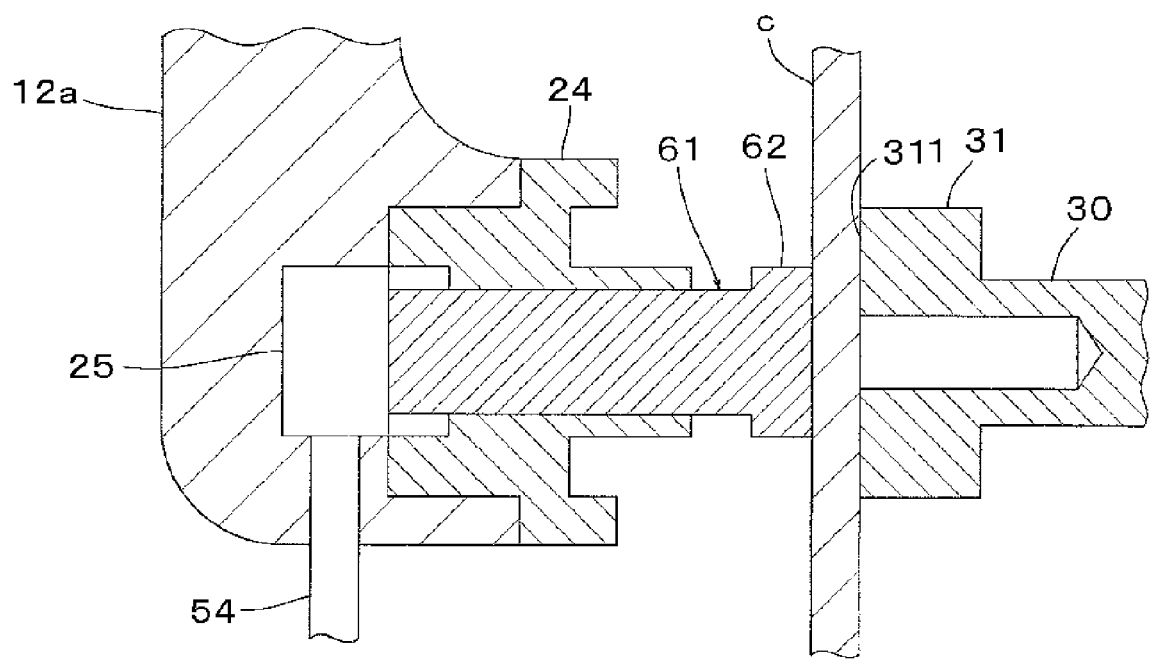
FIG. 10 is a sectional explanation view showing a measuring member in use which has only a cloth thickness measuring portion.

FIG. 10 is a sectional explanation view showing the measuring member 61 in use. The measuring member 61 is fixed to the stationary section fixing part 18 of the front frame 12 via the attachment 24. By an operator griping the operation lever 41, the mover 30 moves forward, and then the pushing surface 311 of the pusher 31 pushes the cloth part c1 against the cloth thickness measuring portion 62 of the measuring member 61. Thereby, the cloth c is compressed becoming thinner gradually. At the time of this compression, the load being applied to the measuring member 61 and the amount of displacement of the mover 30 are detected respectively by the load cell 25 and the pulse code 161. Then, the thickness of the cloth c at the time of when the compressing load reaches the predetermined value (for example, 200 N) is rated as the cloth thickness.

Figure 11:
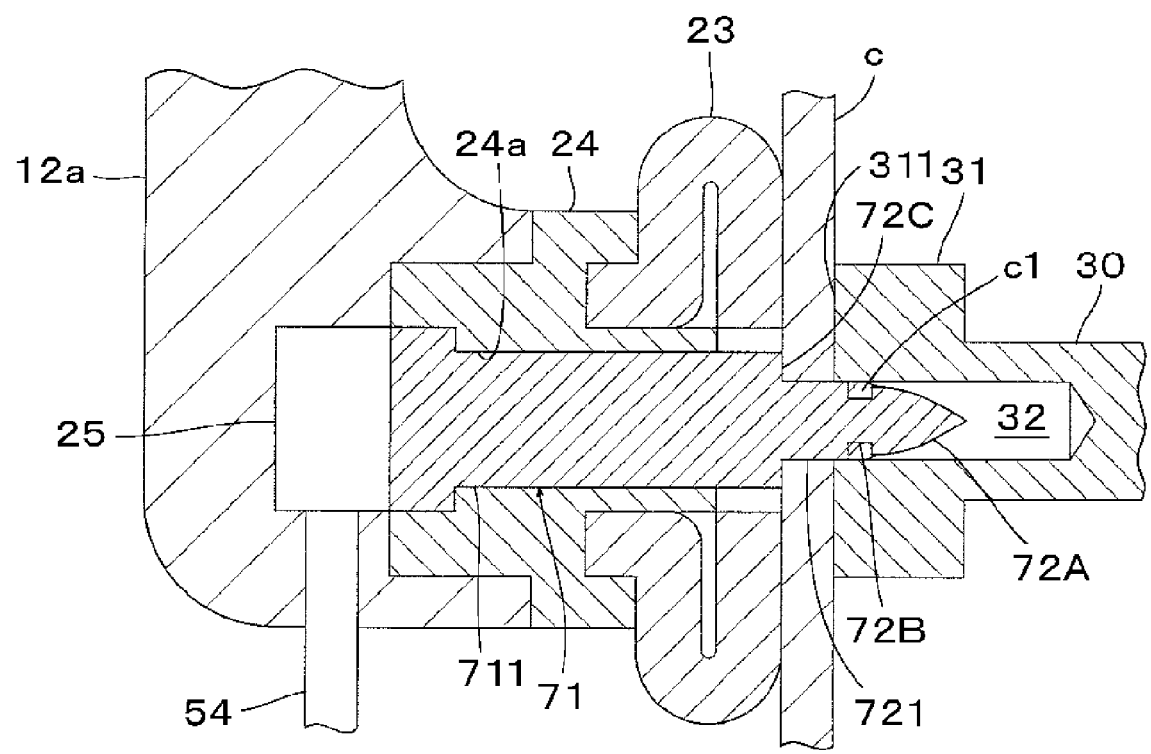
FIG. 11 is a sectional explanation view showing the measuring member in use which has the piercing force measuring portion, the cutting force measuring portion and the cloth thickness measuring portion.

FIG. 11 is a sectional explanation view showing still another measuring member 71 in use. The measuring member 71 includes a piercing force measuring portion 72A and a cutting force measuring portion 72B, which are similar to the piercing force measuring portion 22A and the cutting force measuring portion 22B of the measuring member 21, respectively. However, a proximal portion 711 of the measuring member 71 corresponding to the proximal portion 211 of the measuring member 21 further extends on the distal side, and accordingly a measuring part-proximal portion 721 corresponding to the measuring part-proximal portion 221 of the measuring member 21 is made short in the axial direction. Therefore, the stepped boundary between the measuring part-proximal portion 72' and the proximal portion 711 is positioned on the distal side rather than the distal surface of the measuring member supporting part 24a of the attachment 24. Then, this boundary can serve as a cloth thickness measuring portion 72C to compress the cloth c without passing through the cloth c. With the measuring member 71, the pulling force with the cloth c can be measured by the piercing force measuring portion 72A, and then the cutting force with the cloth c can be measured by the cutting force measuring portion 72B, and after that the cloth thickness can be measured by the cloth thickness measuring portion 72C compressing the cloth c.

Figure 12:
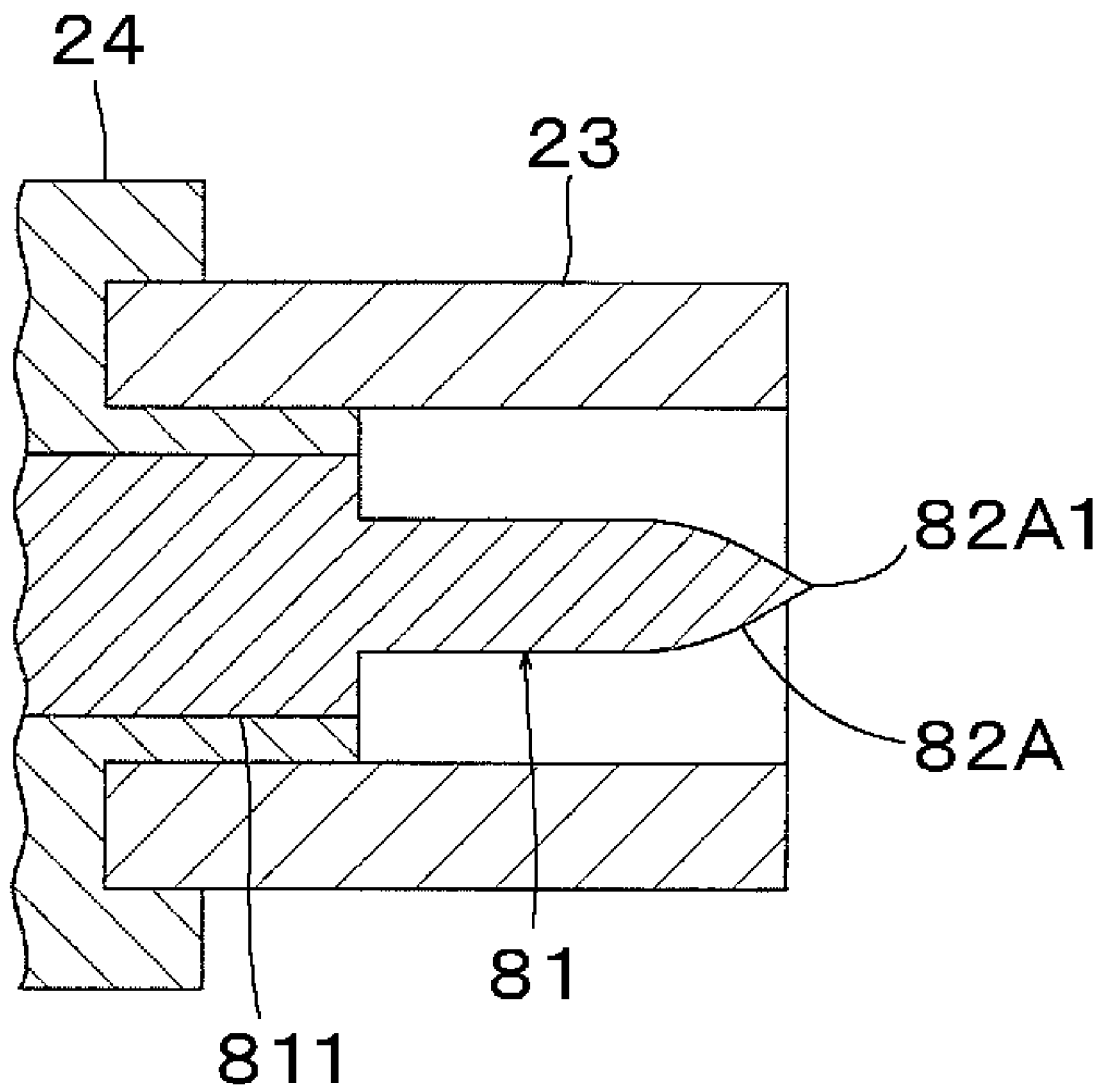
FIG. 12 is a sectional explanation view showing a measuring member having only a piercing force measuring portion.
Figure 13:
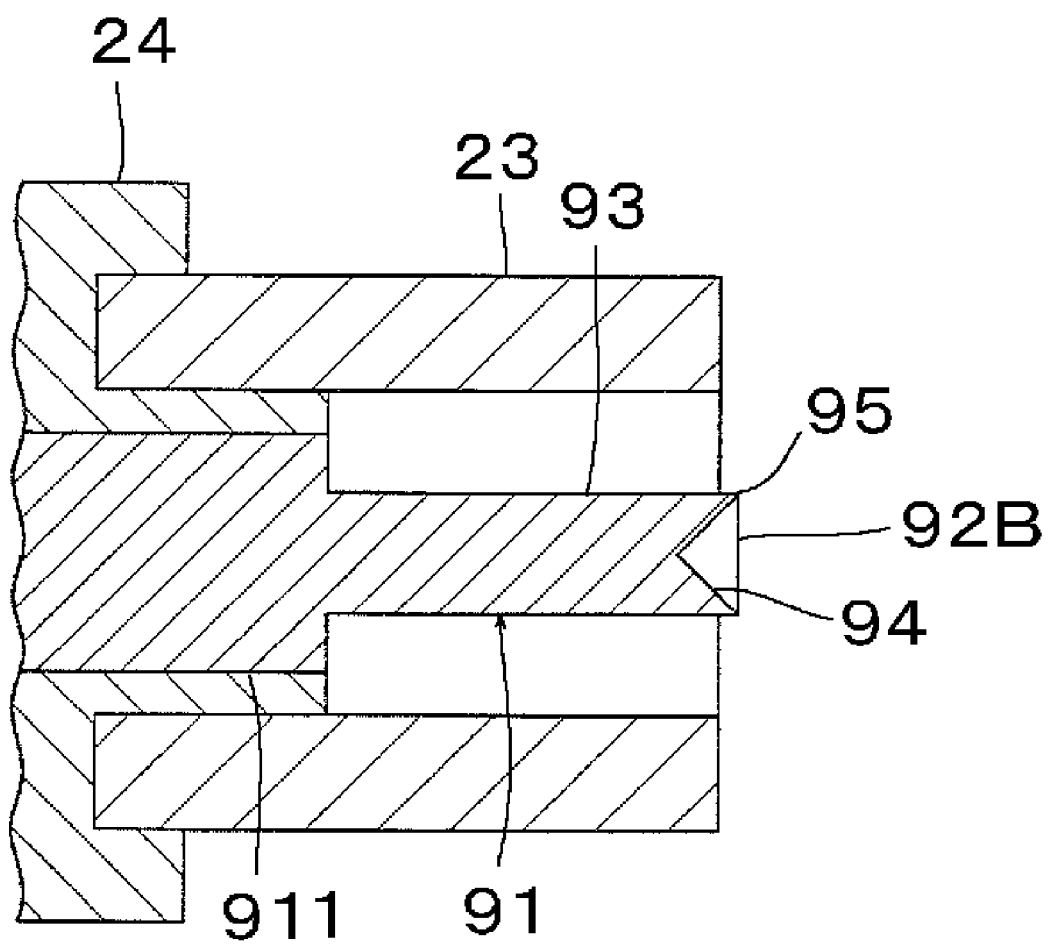
FIG. 13 is a sectional explanation view showing a measuring member having only a cutting force measuring portion.
Figure 14:
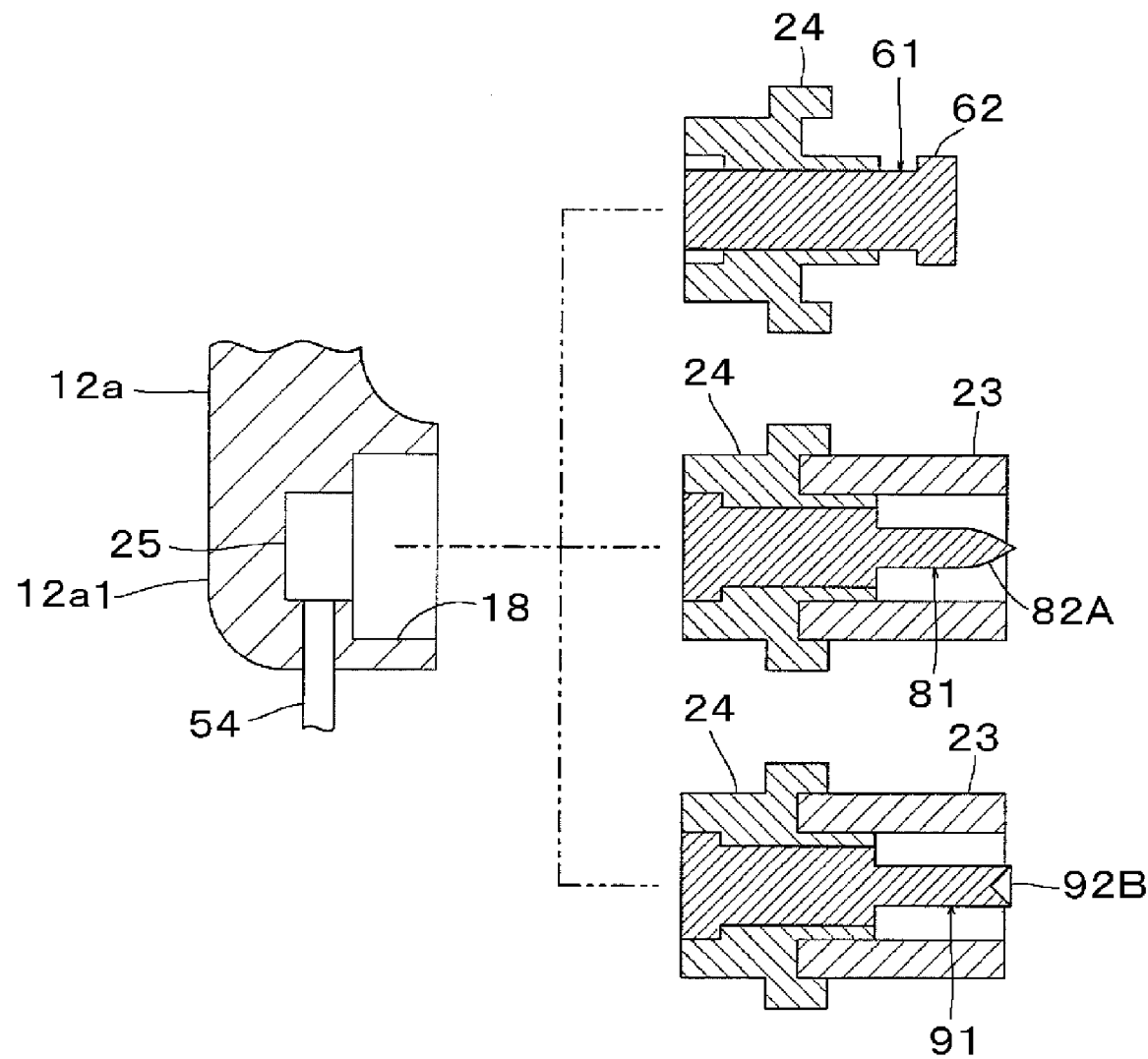
FIG. 14 is a sectional explanation view showing three kinds of measuring members which can be exchangeably mounted to the stationary section fixing part via the attachment.

FIG. 12 is a sectional explanation view partially showing a measuring member 81 which has only a piercing force measuring portion 82A. The outer diameter of the piercing force measuring portion 82A gradually expands proximally from the acute tip 82A1 and then becomes constant to a proximal portion 811. The elastic member 23 and the attachment 24 are the same as those shown in FIG. 2 etc. (the same is true of FIG. 13) FIG. 13 is a sectional explanation view partially showing a measuring member 91 having only a cutting force measuring portion 92B. The cutting force measuring portion 92B is formed to include a column portion 93 which protrudes distally and is decreased in diameter from the proximal portion 911 of the measuring member 91. The distal end of the column portion 93 is formed to be a cone-shaped hollow as a concave surface 94. In the cutting force measuring portion 92B, the concave surface 94 can function as a shear face to push the cloth c, and the peripheral edge of the concave surface 94 becomes an acute edge 95 with less than 90° in cross section to cut a part c1 of the cloth c. The measuring member 81 exclusively for measuring the pulling force in FIG. 12, the measuring member 91 exclusively for measuring the cutting force in FIG. 13 and the measuring member 61 exclusively for measuring the cloth thickness in FIG. 10 etc. are exchangeably mounted the stationary section fixing part 18 of the front frame 12 via the same attachment 24, as shown in FIG. 14.

Figure 15:
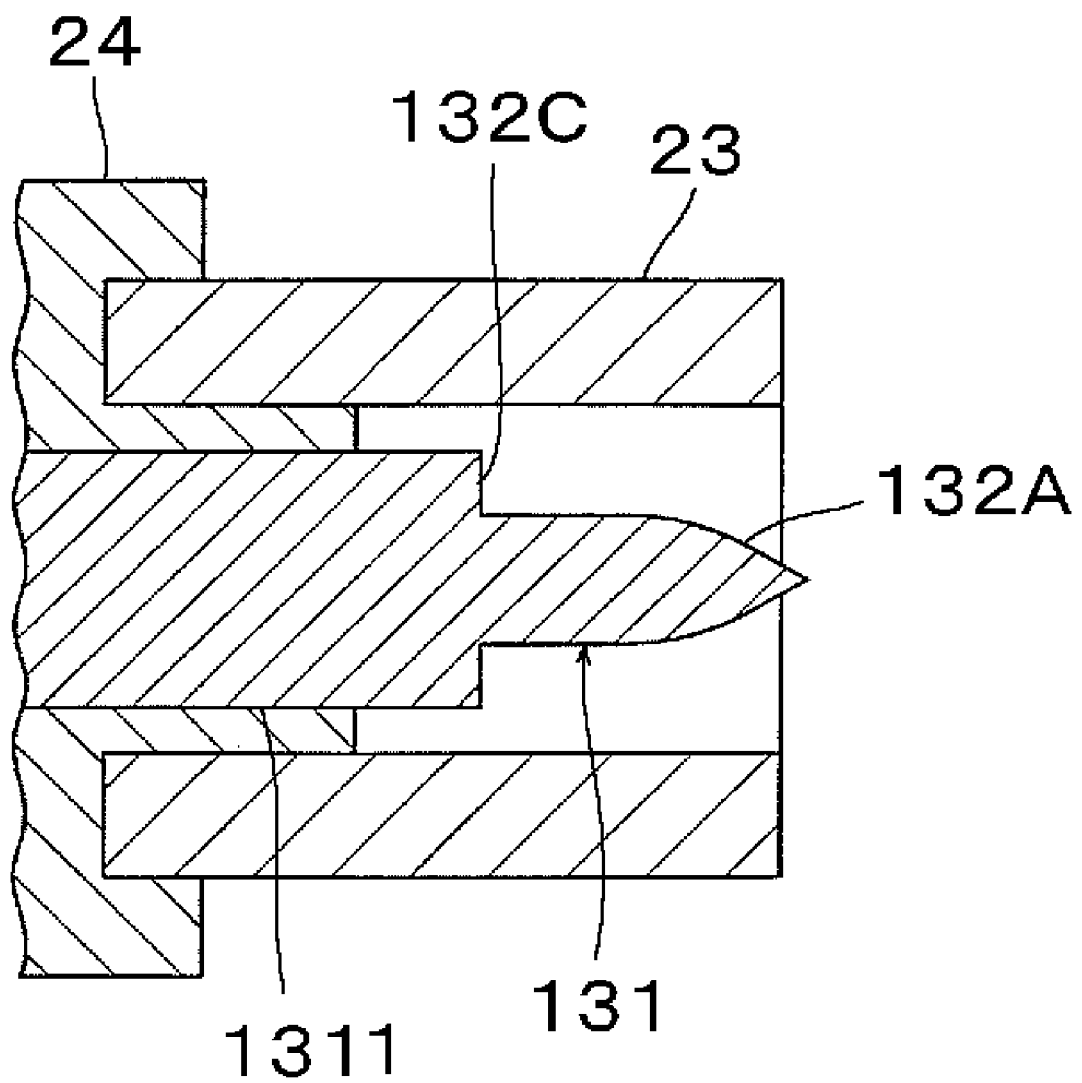
FIG. 15 is a sectional explanation view showing a measuring member which has a piercing force measuring portion and a cloth thickness measuring portion.
Figure 16:
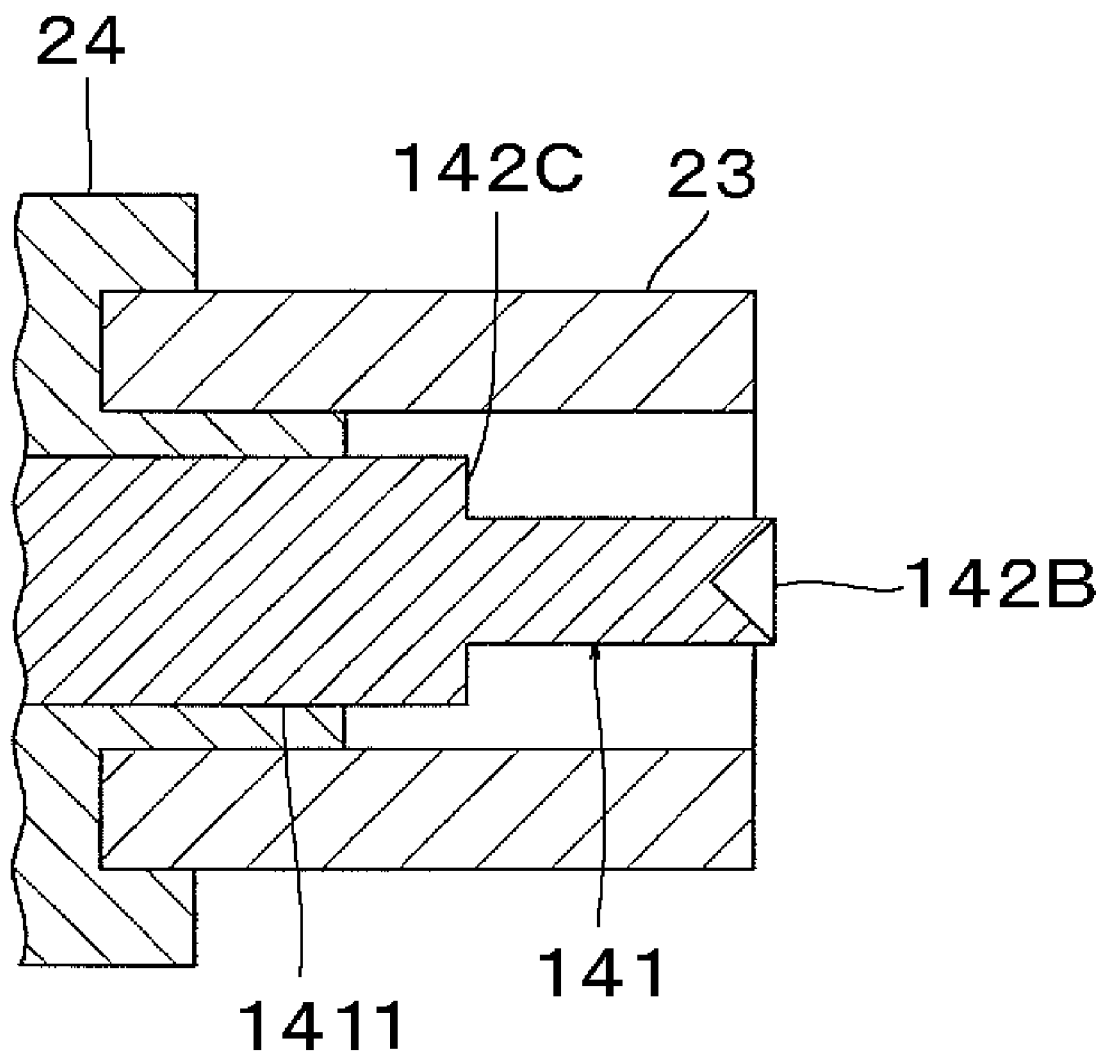
FIG. 16 is a sectional explanation view showing a measuring member which has a cutting force measuring portion and a cloth thickness measuring portion.

FIG. 15 shows another example of a measuring member. This measuring member 131 includes a piercing force measuring portion 132A similar to the piercing force measuring portion 82A of the measuring member 81 shown in FIG. 12 and a cloth thickness measuring portion 132C similar to the cloth thickness measuring portion 72C of the measuring member 71 shown in FIG. 11. However, the measuring member 131 does not have a cutting force measuring portion. The reference numeral 1311 indicates a proximal portion of the measuring member 131. FIG. 16 shows still another example of the measuring member. This measuring member 141 includes a cutting force measuring portion 142B similar to the cutting force measuring portion 92B of the measuring member 91 shown in FIG. 13 and a cloth thickness measuring portion 142C similar to the cloth thickness measuring portion 72C of the measuring member 71 shown in FIG. 11. However, the measuring member 141 does not have a piercing force measuring portion. A reference numeral 1411 indicates a proximal portion of the measuring member 141.

Figure 17:
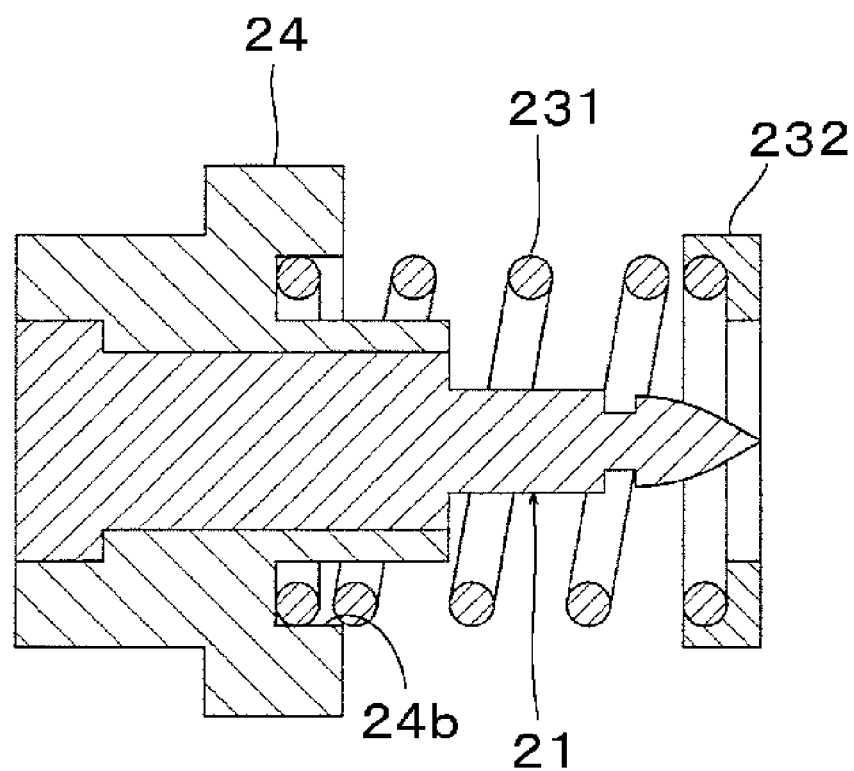
FIG. 17 is a sectional explanation view showing another example of an elastic member.

FIG. 17 shows another example of the elastic member. The measuring member 21 and the attachment 24 are substantially the same as those shown in FIG. 2 etc., so the same reference numerals are used. An elastic member 231 is constituted by a coil spring. The proximal portion of the elastic member 231 is supported by the elastic member receiving part 24b of the attachment 24, and an annular cloth support member 232 is attached to the distal end of the elastic member 231. The elastic member 231 can support the cloth c by pushing the cloth support member 232 at around a passing-through point on the first surface ca of the cloth c as the measuring part 22 of the measuring member 21 passes through the cloth c.

Figure 18:
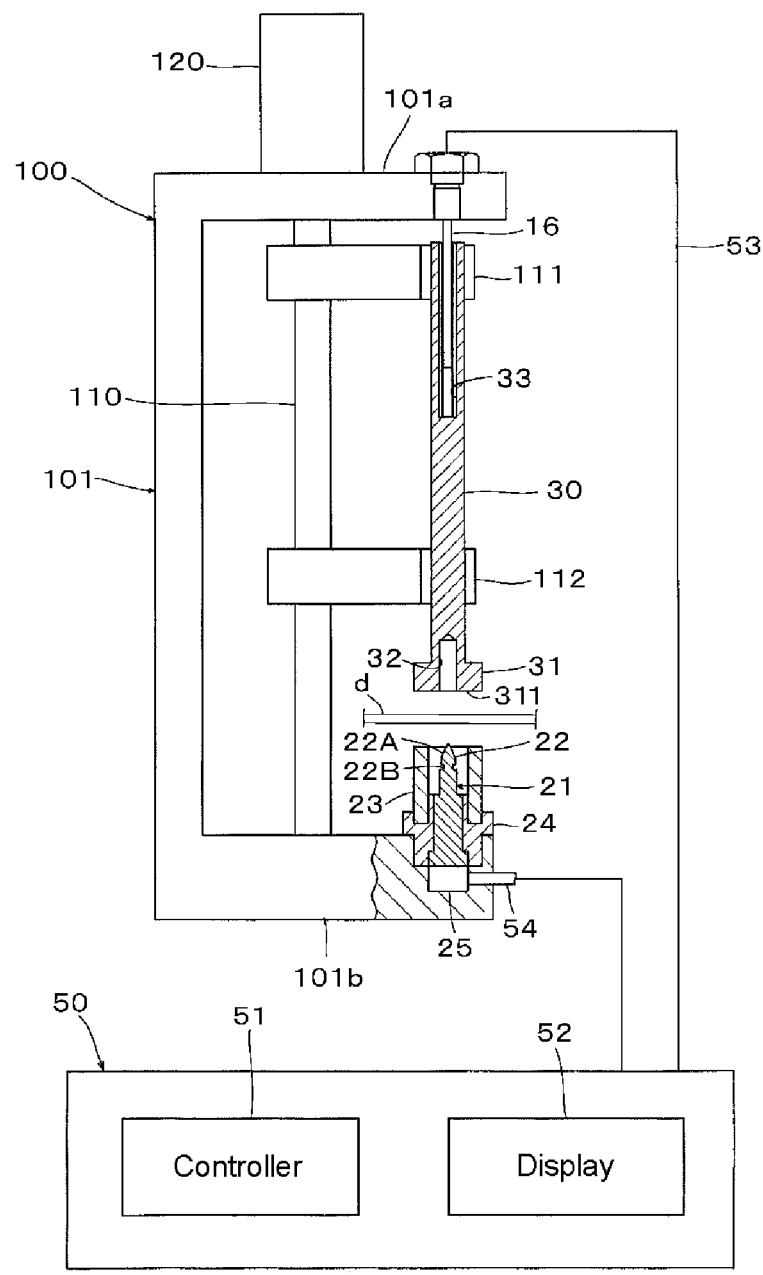
FIG. 18 is a partially sectional explanation view schematically showing another embodiment of the measuring apparatus.

FIG. 18 shows another example of a measuring unit 100 in the cloth evaluation apparatus in accordance with the present invention. Concerning substantially the same constructions as those in the cloth evaluation apparatus 1 as stated above, specifically, the spline shaft 16 including the pulse coder 161, the measuring member 21, the elastic member 23, the stationary section 20 including the load cell 25 etc., the mover 30 including the pusher 31 etc., the control box 50 including the controller 51 etc., and the signal lines 53, 54 and so on, the same reference numerals are used, and their explanations are omitted. Left and right directions, and upper and lower directions are based on FIG. 15. The measuring unit 100 includes a frame body 101 which is a U-shaped body facing to the right. At the right end of a lower arm 101b of the frame body 101, the measuring member 21 is disposed such that the tip 22A1 of the measuring part 22 faces upwardly. The mover 30 is supported, via an upper drive transmitter 111 and a lower drive transmitter 112, by a ball screw (feed screw) 110 which is vertically disposed between an upper arm 101a and the down arm 101b of the frame body 101. The ball screw 110 has a male screw (not shown) on the outer surface. Each of the upper and lower drive transmitters 111, 112 has, on the left side, an opening through which the ball screw 110 passes, each opening has a female screw (not shown) to be engaged with the male screw of the ball screw 110. The spline shaft 16 is provided so as to extend downward from the right end of the upper arm 101*a*. A reference numeral 120 indicates a motor that can rotate the ball screw 110 in one and the other directions. At the time of measuring, a cloth d is placed horizontally between the stationary section 20 and the mover 30. After that, the motor 120 is rotated in the one direction. Thereby, the ball screw 110 is rotated in the one direction, and then the upper and lower drive transmitters 111, 112 are moved downward, lowering the mover 30 from the initial position in FIG. 18. Thereby, the pusher 31 pushes the cloth d against the measuring part 22 of the measuring member 21, and the piercing force measuring portion 22A and then the cutting force measuring portion 22B pass through the cloth d upward. At this time, the load being applied to the measuring member 21 and the displacement amount of the mover 30 are detected by the load cell 25 and the pulse coder 161, respectively and sent to the controller 51. After the measurements are done, as the motor 120 is rotated in the other direction, the mover 30 can be lifted to return to the initial position.

DESCRIPTION OF REFERENCE NUMBERS c, d cloth
1 cloth evaluation apparatus
10, 100 measuring unit
11 frame body
161 pulse coder
20 stationary section
21, 61, 71, 81, 91, 131 141 measuring member
22 measuring part
22A, 72A, 82A, 132A piercing force measuring portion
22A1, 82A1 tip
22A2 piercing force measuring portion
22B, 72B, 92B, 142B cutting force measuring portion
22Ba depression
22Bb, 94 shear face
22Bc, 95 edge
23, 231 elastic member
24 attachment
25 load cell
30 mover
31 pusher
311 pushing surface
32 cavity
40 mover driving mechanism
41 operation lever
50 control box
41 controller
52 display
62, 72C, 132C, 142C cloth thickness measuring portion

The invention claimed is:

1. A cloth evaluation apparatus comprising:
a first section, comprising:
  a measuring member having, on its distal side, a measuring part to pass through a cloth, wherein the measuring part includes a piercing force measuring portion and an outer diameter of the piercing force measuring portion gradually decreases toward its acute tip;
  a cylindrical elastic member arranged around the measuring part of the measuring member, wherein the elastic member is configured to support a first side of the cloth; and
  a load cell capable of detecting a load applied to the measuring member; and
a second section, comprising:
  a pusher, wherein the pusher has a pushing surface and a cavity for receiving the piercing force measuring portion, and the pushing surface is configured to support a second side of the cloth,
  wherein the elastic member is compressed in its axial direction when the piercing force measuring portion is moved into the cavity.

2. The cloth evaluation apparatus according to claim 1, including a displacement sensor for detecting a displacement amount of the measuring part with respect to the cloth.

3. A cloth evaluation apparatus comprising:
a first section, comprising:
  a measuring member having, on its distal side, a measuring part to pass through a cloth, wherein the measuring part includes a cutting force measuring portion having a shear face;
  a cylindrical elastic member arranged around the measuring part of the measuring member, wherein the elastic member is configured to support a first side of the cloth; and
  a load cell capable of detecting a load applied to the measuring member; and
a second section, comprising:
  a pusher, wherein the pusher has a pushing surface and a cavity for receiving the cutting force measuring portion, and the pushing surface is configured to support a second side of the cloth,
  wherein the elastic member is compressed in its axial direction when the cutting force measuring portion is moved into the cavity.

4. The cloth evaluation apparatus according to claim 3, including a displacement sensor for detecting a displacement amount of the measuring part with respect to the cloth.

5. A cloth evaluation apparatus comprising:
a first section, comprising:
  a measuring member having, on its distal side, a measuring part to pass through a cloth, wherein the measuring part includes a piercing force measuring portion having an outer diameter which gradually decreases toward an acute tip of the piercing force measuring portion and a cutting force measuring portion adjacent proximally to the piercing force measuring portion, the cutting force measuring portion having a shear face;
  an elastic member arranged around the measuring part of the measuring member, wherein the elastic member is configured to support a first side of the cloth; and
  a load cell capable of detecting a load applied to the measuring member; and
a second section, comprising:
  a pusher, wherein the pusher has a pushing surface and a cavity for receiving the measuring part, and the pushing surface is configured to support a second side of the cloth,
  wherein the elastic member is compressed when the measuring part is moved into the cavity.

6. The cloth evaluation apparatus according to claim 5, wherein the cutting force measuring portion includes an annular depression with a decreased outer diameter between the proximal end of the piercing force measuring portion and the shear face, the outer diameter of the proximal end being maximum in the piercing force measuring portion, and a surface, in the annular depression, on the proximal side of the measuring member serves as the shear face.

7. The cloth evaluation apparatus according to claim 6, including a displacement sensor for detecting a displacement amount of the measuring part with respect to the cloth.

8. The cloth evaluation apparatus according to claim 5, including a displacement sensor for detecting a displacement amount of the measuring part with respect to the cloth.

9. The cloth evaluation apparatus according to claim 5, wherein the measuring part includes a cloth thickness measuring portion, to compress the cloth, proximally from the cutting force measuring portion.

10. A cloth evaluation apparatus comprising:
   a first section, comprising:
      a measuring member having, on its distal side, a measuring part to pass through or compress a cloth, wherein as the measuring member, a first measuring member and a second measuring member can be exchangeably used, wherein the measuring part of the first measuring member is a piercing force measuring portion having an outer diameter which gradually decreases toward an acute tip of the piercing force measuring portion, and the measuring part of the second measuring member is a cutting force measuring portion having a shear face;
      an elastic member arranged around the measuring part of the measuring member, wherein the elastic member is configured to support a first side of the cloth;
      a load cell capable of detecting a load applied to the measuring member; and
      an attachment for supporting the measuring member and the elastic member; and
   a second section, comprising:
      a pusher, wherein the pusher has a pushing surface and a cavity for receiving the piercing force measuring portion or the cutting force measuring portion, and the pushing surface is configured to support a second side of the cloth; and
      a displacement sensor for detecting a displacement amount of the measuring part with respect to the cloth;
   wherein the elastic member is compressed when the piercing force measuring portion or the cutting force measuring portion is moved into the cavity.

11. The cloth evaluation apparatus according to claim 10, wherein as the measuring member, the first measuring member, the second measuring member and a third measuring member can be exchangeably used, and the measuring part of the third measuring member is a cloth thickness measuring portion to compress the cloth.

12. A cloth evaluation apparatus comprising:
   a first section, comprising:
      a measuring member having, on its distal side, a measuring part to pass through or compress a cloth, wherein as the measuring member, a first measuring member and a second measuring member can be exchangeably used, wherein the measuring part of the first measuring member includes a piercing force measuring portion having an outer diameter which gradually decreases toward an acute tip of the piercing force measuring portion and a cutting force measuring portion adjacent proximally to the piercing force measuring portion, the cutting force measuring portion having a shear face, wherein the measuring part of the second measuring member is a cloth thickness measuring portion, to compress the cloth;
      an elastic member arranged around the measuring part of the measuring member, wherein the elastic member is configured to support a first side of the cloth; and
      a load cell capable of detecting a load applied to the measuring member; and
   a second section, comprising:
      a pusher, wherein the pusher has a pushing surface and a cavity for receiving the piercing force measuring portion or the cutting force measuring portion, and the pushing surface is configured to support a second side of the cloth,
      a displacement sensor for detecting a displacement amount of the measuring part with respect to the cloth;
   wherein the elastic member is compressed when the piercing force measuring portion is moved into the cavity.

* * * * *

UNITED STATES PATENT AND TRADEMARK OFFICE
CERTIFICATE OF CORRECTION

PATENT NO.         : 9,074,973 B2
APPLICATION NO.    : 13/814376
DATED              : July 7, 2015
INVENTOR(S)        : Kenji Hasegawa et al.

It is certified that error appears in the above-identified patent and that said Letters Patent is hereby corrected as shown below:

In the Specification

In column 1, line 11-12, delete "preliminary" and insert -- preliminarily --, therefor.

In column 1, line 30, delete "preliminary" and insert -- preliminarily --, therefor.

In column 8, line 41, delete "portion211" and insert -- portion 211 --, therefor.

In column 11, line 43, delete "72" and insert -- 721 --, therefor.

In column 13, line 50, delete "41" and insert -- 51 --, therefor.

Signed and Sealed this
Twenty-ninth Day of December, 2015

Michelle K. Lee
*Director of the United States Patent and Trademark Office*